(12) United States Patent
Suyama et al.

(10) Patent No.: US 8,723,129 B2
(45) Date of Patent: May 13, 2014

(54) SCINTILLATOR PLATE

(75) Inventors: Toshiyasu Suyama, Hamamatsu (JP); Mototsugu Sugiyama, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 13/981,425

(22) PCT Filed: Oct. 21, 2011

(86) PCT No.: PCT/JP2011/074335
§ 371 (c)(1), (2), (4) Date: Oct. 7, 2013

(87) PCT Pub. No.: WO2012/101884
PCT Pub. Date: Aug. 2, 2012

(65) Prior Publication Data
US 2014/0021372 A1    Jan. 23, 2014

(30) Foreign Application Priority Data
Jan. 25, 2011   (JP) .................................. 2011-013206

(51) Int. Cl.
*G01T 1/20* (2006.01)
*G01J 1/58* (2006.01)

(52) U.S. Cl.
USPC ..................... 250/367; 250/361 R; 250/486.1

(58) Field of Classification Search
USPC ....... 250/361 R, 362, 366, 367, 458.1, 459.1, 250/483.1, 484.2, 484.4, 486.1, 487.1
See application file for complete search history.

(56) References Cited

U.S. PATENT DOCUMENTS 7,405,406 B1   7/2008   Nagarkar et al.

FOREIGN PATENT DOCUMENTS

| JP | S61-95299 A | 5/1986 |
| JP | 2002-301054 A | 10/2002 |
| JP | 2007-139604 A | 6/2007 |

*Primary Examiner* — Mark R Gaworecki
(74) *Attorney, Agent, or Firm* — Drinker Biddle & Reath LLP

(57) ABSTRACT

This scintillator plate 1 is a scintillator plate which is a member of a flat plate shape to emit scintillation light according to incidence of radiation transmitted by an object A and which is used in an image acquisition device to condense and image the scintillation light, the scintillator plate comprising: a partition plate 2 of a planar shape which transmits radiation; a scintillator 3 of a flat plate shape which is arranged on one surface 2a of the partition plate 2 and which converts the radiation into scintillation light; and a scintillator 4 of a flat plate shape which is arranged on the other surface 2b of the partition plate 2 and which converts the radiation into scintillation light.

6 Claims, 6 Drawing Sheets

SCINTILLATOR PLATE

TECHNICAL FIELD

The present invention relates to a scintillator plate for converting radiation transmitted by an object, into scintillation light.

BACKGROUND ART

The conventionally known technologies for detection of X-ray images include a direct conversion method which is a method of detecting charge produced by radiation incident into a detector, thereby to directly detect the radiation, and an indirect conversion method which is a method of converting the radiation into light by means of a radiation conversion member such as a scintillator material and detecting the light by a detector. A scintillator plate with a fluorescent panel having a phosphor layer formed on a substrate is disclosed as a scintillator used in apparatus employing the aforementioned indirect conversion method (cf. Patent Literature 1 below).

CITATION LIST

Patent Literature

Patent Literature 1: Japanese Patent Application Laid-open No. 2007-139604

SUMMARY OF INVENTION

Technical Problem

In the case of the conventional scintillator plate as described above, however, since the substrate is present on one side of the phosphor layer, it was difficult to observe the scintillation light emitted from both of a radiation entrance surface and a back surface behind it. Namely, it is hard to observe the scintillation light generated on the back side of the phosphor layer by radiation in a relatively high energy band. Even if we can successfully observe the scintillation light emitted from the back surface side of the scintillator plate, the scintillation light generated on the entrance surface side of the scintillator plate will also be transmitted by the scintillator plate and emitted from the back surface side thereof. Therefore, the conventional technologies failed to separately observe the scintillation light generated on the entrance surface side of the phosphor layer by radiation in a relatively low energy band and the scintillation light generated on the back surface side of the phosphor layer by radiation in a relatively high energy band, and therefore they tended to have an insufficient energy separation capability of observed radiation.

The present invention has been accomplished in view of the above-described problem and it is an object of the present invention to provide a scintillator plate enabling observation of scintillation light emitted from a radiation entrance surface and a back surface behind it, thereby enabling acquisition of radiation detection images with a high energy separation capability.

Solution to Problem

In order to solve the above problem, a scintillator plate according to one aspect of the present invention is a scintillator plate which is a member of a flat plate shape to emit scintillation light according to incidence of radiation transmitted by an object and which is used in an image acquisition device to condense and image the scintillation light, the scintillator plate comprising: a partition member of a planar shape which transmits radiation; a first wavelength conversion member of a flat plate shape which is arranged on one surface of the partition member and which converts the radiation into scintillation light; and a second wavelength conversion member of a flat plate shape which is arranged on the other surface of the partition member and which converts the radiation into scintillation light.

In this scintillator plate, the two wavelength conversion members of the flat plate shape to convert the radiation into scintillation light are arranged on both sides of the partition member of the planar shape which transmits the radiation; therefore, one wavelength conversion member converts the radiation transmitted by the object, into scintillation light and the other wavelength conversion member converts the radiation transmitted by the one wavelength conversion member and the partition member, into scintillation light. At this time, the existence of the partition member makes the scintillation light beams generated respectively by the two wavelength conversion members, easier to be emitted from the respective surfaces of the two wavelength conversion members on the opposite sides with respect to the partition member. As a result, when this scintillator plate is used in the image acquisition device to condense and image the scintillation light beams emitted from the two surfaces of the scintillator plate, it can efficiently separate the high-energy radiation image and the low-energy radiation image.

Advantageous Effect of Invention

The present invention enables observation of the scintillation light beams emitted from the radiation entrance surface and the back surface behind it, thereby enabling acquisition of radiation detection images with a high energy separation capability.

DESCRIPTION OF EMBODIMENTS

Figure 1:
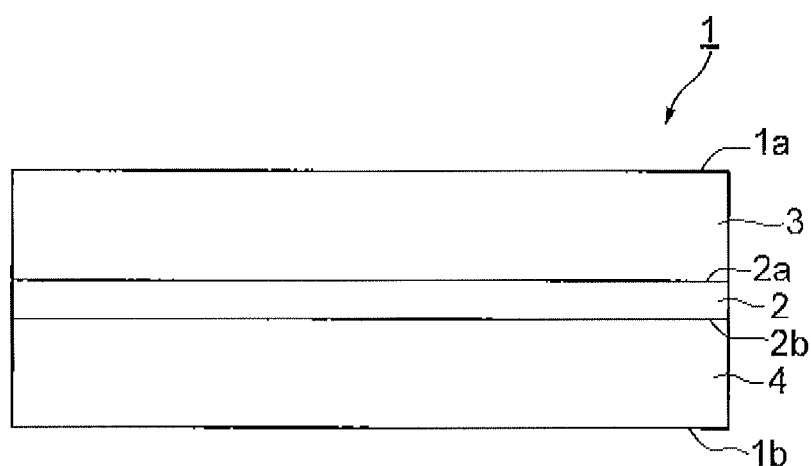
FIG. 1 is a front view showing a schematic configuration of a scintillator plate 1 according to a preferred embodiment of the present invention.

Preferred embodiments of the scintillator plate according to the present invention will be described below in detail with reference to the drawings. Identical or equivalent portions will be denoted by the same reference signs in the description of the drawings, without redundant description. It is noted that each drawing is prepared by way of illustration only and is depicted so as to emphasize each part as object of description in particular. For this reason, the dimensional ratios of respective members in the drawings are not always coincident with actual ones.

FIG. 1 is a front view showing a schematic configuration of a scintillator plate 1 according to a preferred embodiment of the present invention. As shown in the same drawing, the scintillator plate 1 is a member that converts radiation such as X-rays transmitted by an object, into scintillation light, and is configured so that two scintillators 3, 4 of a flat plate shape are arranged in contact with two surfaces of a partition plate (partition member) 2 of a planar shape.

The scintillators 3, 4 are wavelength conversion members that generate scintillation light according to incidence of radiation, materials of which are selected depending upon energy bands of radiation to be detected and thicknesses of which are also set to appropriate values depending upon the energy bands of radiation to be detected, in the range of several μm to several mm. For example, the materials of the scintillators 3, 4 to be used herein are selected from $Gd_2O_2S:Tb$, $Gd_2O_2S:Pr$, CsI:Tl, $CdWO_4$, $CaWO_4$, $Gd_2SiO_5:Ce$, $Lu_{0.4}Gd_{1.6}SiO_5$, $Bi_4Ge_3O_{12}$, $Lu_2SiO_5:Ce$, $Y_2SiO_5$, $YAlO_3:Ce$, $Y_2O_2S:Tb$, $YTaO_4:Tm$, and so on.

The two scintillators 3, 4 may be made of the same material or of different materials. When they are made of different materials, they are set to have different conversion efficiencies for wavelengths of radiation. For example, the materials of the scintillators 3, 4 can be any one of combinations such as $Gd_2O_2S:Tb$ and CsI:Tl, $Gd_2O_2S:Tb$ and $CdWO_4$, or, CsI:Tl and $CdWO_4$. The two scintillators 3, 4 may be formed in the same thickness or in different thicknesses. When they are formed in different thicknesses, it becomes feasible to adjust sensitivities to radiation transmitted by the two scintillators 3, 4 and response characteristics to wavelengths relative to each other. For example, the thickness of the scintillator 3 can be set in the range of several μm to 300 μm and the thickness of the scintillator 4 can be set in the range of 150 μm to several mm to be thicker than the scintillator 3.

The partition plate 2 is a member of a planar shape in the thickness of 0.5 μm to 5 mm for supporting the scintillators 3, 4, which has two planes 2a, 2b in contact with the two scintillators 3, 4, respectively, and which has a property of transmitting radiation as an object to be detected, and blocking scintillation light generated by the scintillators 3, 4. This partition plate 2 to be used herein is, for example, a carbon plate, a glass plate member such as an FOP (Fiber Optic Plate), an aluminum plate, a beryllium plate, a metal plate member of titanium, gold, silver, iron, or the like, or a resin plate member such as a plastic plate.

The scintillator plate 1 of the above configuration is manufactured by joining plate members on which the respective scintillators 3, 4 are arranged, to each other on the side opposite to the scintillator plates 3, 4. In this case, the scintillator plate can be manufactured with relative ease. The scintillator plate 1 may also be manufactured by placing the scintillators 3, 4 respectively on both sides of the partition plate 2 of a single layer structure.

The below will describe a configuration of a radiation image acquisition device for acquiring a radiation image of an object A, e.g., an electronic component such as a semiconductor device, or a foodstuff, using the scintillator plate 1 of the present embodiment.

Figure 2:
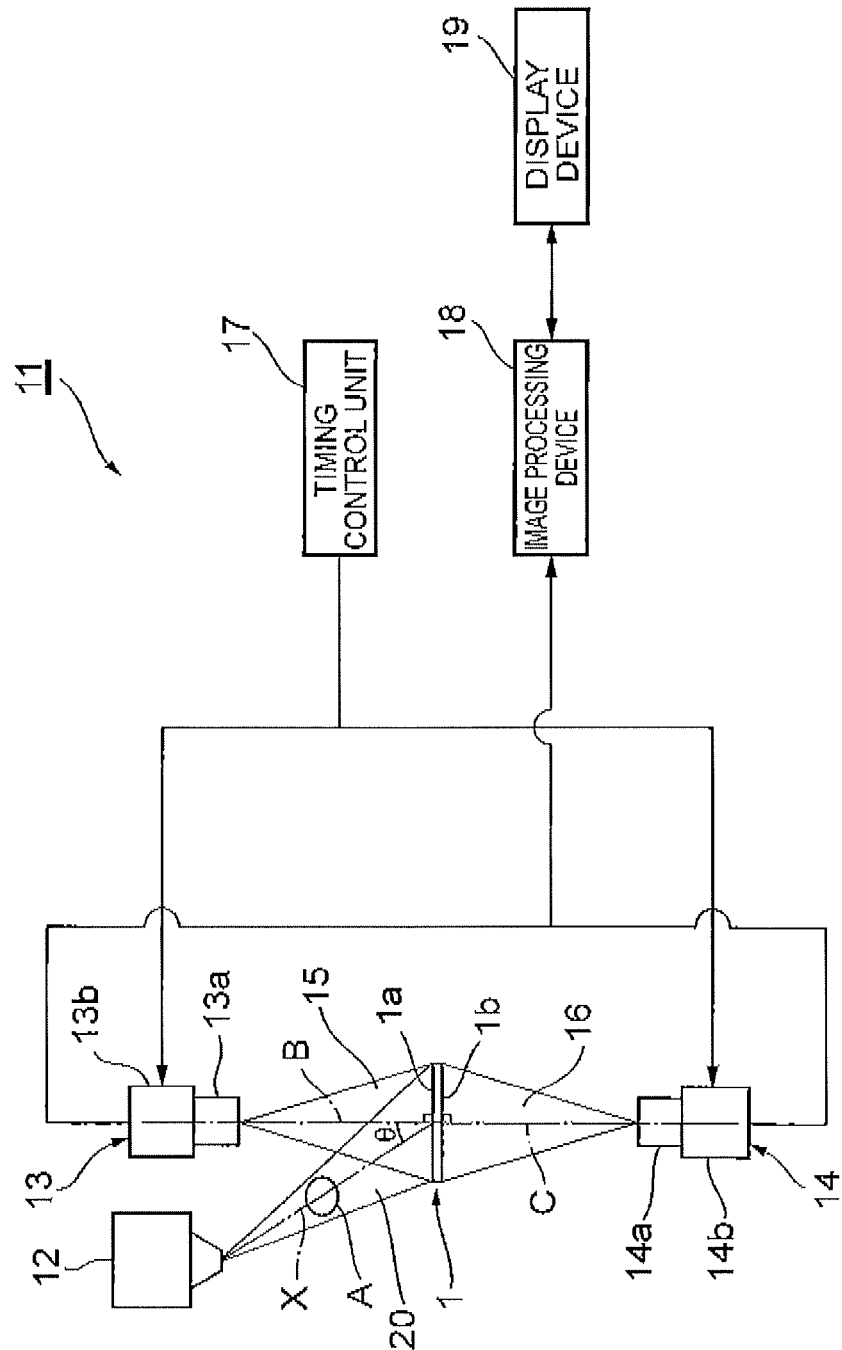
FIG. 2 is a schematic configuration diagram of a radiation image acquisition device 11 using the scintillator plate 1 shown in FIG. 1.

FIG. 2 is a schematic configuration diagram of the radiation image acquisition device 11 using the scintillator plate 1. As shown in the same drawing, the radiation image acquisition device 11 is provided with a radiation source 12 which emits radiation such as white X-rays toward the object A, the scintillator plate 1 which generates scintillation light according to incidence of the radiation transmitted by the object A after emitted from the radiation source 12, a front observation photodetector 13 which condenses and images the scintillation light emitted from the radiation-incidence-side detection surface 1a of the scintillator plate 1, and a back observation photodetector 14 which condenses and images the scintillation light emitted from the detection surface 1b being the surface opposite to the detection surface 1a. The scintillator plate 1 is arranged in a state in which the detection surface 1a of the scintillator 3 faces the object A. Namely, the scintillator plate 1 is so arranged that the surface 1a of the scintillator 3 opposite to the partition plate 2 is opposed to the front observation photodetector 13 and that the surface 1b of the scintillator 4 opposite to the partition, plate 2 is opposed to the back observation photodetector 14. These radiation source 12, scintillator plate 1, front observation photodetector 13, and back observation photodetector 14 are housed in a housing not shown and fixed in the housing.

The front observation photodetector 13 (which will be referred to hereinafter as "front detector 13") is an imaging device of the indirect conversion method that images the scintillation light emitted from the scintillator plate 1, on the detection surface 1a side of the scintillator plate 1, to acquire a radiation transmission image of relatively low energy of the object A. The front detector 13 is a detector of a lens coupling type having a condensing lens unit 13a for condensing the scintillation light emitted from the detection surface 1a of the scintillator plate 1, and an imaging unit 13b for imaging the scintillation light condensed by the condensing lens unit 13a. The condensing lens unit 13a condenses the scintillation light in a field 15 including a predetermined range on the detection surface 1a. The imaging unit 13b to be used herein is, for example, a CMOS sensor, a CCD sensor, or the like.

The back observation photodetector 14 (which will be referred to hereinafter as "back detector 14") is an imaging device of the indirect conversion method that images the scintillation light emitted from the scintillator plate 1, on the detection surface 1b side of the scintillator plate 1, to acquire a radiation transmission image of relatively high energy of the object A. The back detector 14 is a detector of the lens coupling type having a condensing lens unit 14a for condensing the scintillation light emitted from the detection surface 1b of the scintillator plate 1, and an imaging unit 14b for imaging the scintillation light condensed by the condensing lens unit 14a, and thus it has the same configuration as the aforementioned front detector 13. The condensing lens unit 14a condenses the scintillation light in a field 16 including a predetermined range on the detection surface 1b.

Furthermore, the radiation image acquisition device 11 is provided with a timing control unit 17 for controlling imaging timing at the front detector 13 and at the back detector 14, an image processing device 18 for receiving input image signals output from the front detector 13 and from the back detector 14 and executing a predetermined processing procedure such as image processing based on each of the input image signals, and a display device 19 for receiving an input image signal output from the image processing device 18 and displaying a radiation image. The image processing herein can be, for example, an inter-image operation to create a differential image or an addition image between the input relatively-low-energy image and relatively-high-energy image. The timing control unit 17 and the image processing device 18 are composed of a computer having a CPU (Central Processing Unit), a ROM (Read Only Memory), a RAM (Random Access Memory), input/output interfaces, and so on. The display device 19 to be used herein is a well-known display. The timing control unit 17 and the image processing device 18 may be configured as a program executed by a single computer or as respective units provided individually.

The radiation source 12 is arranged so that the optical axis X of radiation makes a predetermined angle θ (0°<θ<90°) with respect to a normal B to the detection surface 1a of the scintillator plate 1. Namely, the radiation source 12 is located at a position where it faces the object A and the detection surface 1a and is set off the normal B to the detection surface 1a. The normal B here is a straight line extending normally to the detection surface 1a from a certain point on the detection surface 1a.

The front detector 13 is arranged so that the optical axis of the incorporated condensing lens unit 13a is perpendicular to the detection surface 1a, so as to be able to image the scintillation light emitted from the detection surface 1a of the scintillator plate 1. In this configuration, the optical axis of the condensing lens unit 13a is coincident with the normal B to the detection surface 1a. Namely, the front detector 13 faces the detection surface 1a and is arranged on the normal B to the detection surface 1a. This condensing lens unit 13a condenses the scintillation light emitted in the direction of the normal B from the detection surface 1a, toward the imaging unit 13b.

As described above, the front detector 13 is arranged off the optical axis X of the radiation source 12. Namely, the front detector 13 is arranged so as to be located apart from a radiation emission region (region where a radiation beam 20 exists) from the radiation source 12. This arrangement prevents the front detector 13 from being exposed to the radiation from the radiation source 12 and prevents a direct conversion signal of radiation from being produced inside the front detector 13 to generate noise.

Furthermore, the back detector 14 is arranged so that the optical axis of the incorporated condensing lens unit 14a is perpendicular to the detection surface 1b, so as to be able to image the scintillation light emitted from the detection surface 1b of the scintillator plate 1. In this configuration, the optical axis of the condensing lens unit 14a is coincident with a normal C to the detection surface 1b. Namely, the back detector 14 faces the detection surface 1b and is arranged on the normal C to the detection surface 1b. The normal C here is a straight line extending normally to the detection surface 1b from a certain point on the detection surface 1b. In the radiation image acquisition device 11, the normal C is coincident with the normal B. The condensing lens unit 14a condenses the scintillation light emitted in the direction of the normal C from the detection surface 1b, toward the imaging unit 14b.

The following will describe the operation of the radiation image acquisition device 11 having the above-described configuration. First, X-rays are emitted from the radiation source 12 toward the object whereupon the scintillation light emitted from the detection surface 1a becomes light resulting mainly from conversion of low energy components of incident radiation. On the other hand, the scintillation light emitted from the detection surface 1b becomes light resulting mainly from conversion of high energy components of incident radiation. This is because the radiation in the low energy band is likely to be converted into the scintillation light on the detection surface 1a side inside the scintillator 3 of the scintillator plate 1, while the radiation in the high energy band is likely to pass through the scintillator 3 and the partition plate 2 of the scintillator plate 1 and to be converted into the scintillation light near the detection surface 1b inside the scintillator 4. In this connection, the scintillator 3 which faces the object A and converts the radiation in the relatively low energy band is preferably thicker than the scintillator 4 which converts the radiation in the relatively high energy band. In this case, the scintillator 3 is more likely to cut the radiation in the low energy band and the radiation in the higher energy band becomes more likely to be converted into scintillation light on the detection surface 1b side of the scintillator 4; therefore, energy separation of radiation, images acquired by the front detector 13 and the back detector 14 is more improved. When the energy of the radiation source 12 is low overall, the thickness of the scintillator 3 can be decreased to enhance efficiency of conversion of lower energy and increase the transmittance of high-energy radiation, so as to increase the conversion efficiency in the scintillator 4, thereby enhancing the energy separation performance. On the other hand, when the energy of the radiation source 12 is high overall, the thickness of the scintillator 3 can be increased to facilitate conversion of radiation of low energy to middle energy in the scintillator 3 and change a ratio of cutting the radiation in the low energy band, so as to facilitate conversion of radiation in the high energy band in the scintillator 4, thereby improving the energy separation performance.

The timing control unit 17 performs control to make the front detector 13 and the back detector 14 simultaneously carry out their respective imaging operations with the X-ray irradiation as described above. The dual imaging of radiation images of the object A on both of the front and back surfaces is executed based on timing control by the timing control unit 17. In this dual imaging, the front detector 13 acquires the radiation image in the relatively low energy band and the back detector 14 the radiation image in the relatively high energy band. This operation results in acquiring the radiation images in the different energy bands, thus realizing dual energy imaging.

The functions of the front detector 13 and the back detector 14 will be specifically described in more detail; the front detector 13 detects a fluorescent image on the detection surface 1a side. The detection of the fluorescent image on the detection surface 1a side is characterized by little blur of fluorescence and high luminance of fluorescence. This is because the front observation is less affected by blur inside the scintillator plate 1 and by diffusion and self-absorption inside the scintillator plate 1. On the other hand, the back detector 14 detects a fluorescent image formed on the detection surface 1b side after travel in the thickness direction in the scintillator plate 1.

Next, the front detector 13 and the back detector 14 output their respective image signals corresponding to the radiation images on the front and back surfaces, to the image processing device 18. When the image processing device 18 receives the respective input image signals from the front detector 13 and from the back detector 14, the image processing device 18 executes the predetermined processing based on the input image signals and outputs an image signal after the image processing to the display device 19. When the display device 19 receives the input image signal after the image processing from the image processing device 18, the display device 19 displays a radiation image according to the input image signal after the image processing.

In the radiation image acquisition device 11, the radiation source 12 is arranged at the position off the normal B to the detection surface 1a and, the front detector 13 and the back detector 14 are arranged on the normals B and C, respectively; therefore, no detector shadow is cast on the radiation transmission images, so as to suppress generation of noise component and it causes no attenuation of radiation due to the detectors, thus preventing reduction of signal components. Furthermore, the front detector 13 and the back detector 14 are prevented from being exposed to the radiation and generation of noise is suppressed inside the front detector 13. As a consequence, the low-energy image and the high-energy image can be simultaneously acquired by one shot, so as to ensure simultaneity, reduce an exposure dose, decrease an imaging time, and avoid pixel shifts (misregistration). In addition, the front detector 13 and the back detector 14 both can acquire the radiation images without perspective, which facilitates the operation between the images on the detection surface 1a side and on the detection surface 1b side.

It is noted herein that the above-described radiation image acquisition device 11 may be configured with change in positional relationship among the radiation source 12, the front detector 13, and the back detector 14 as described below.

Figure 3:
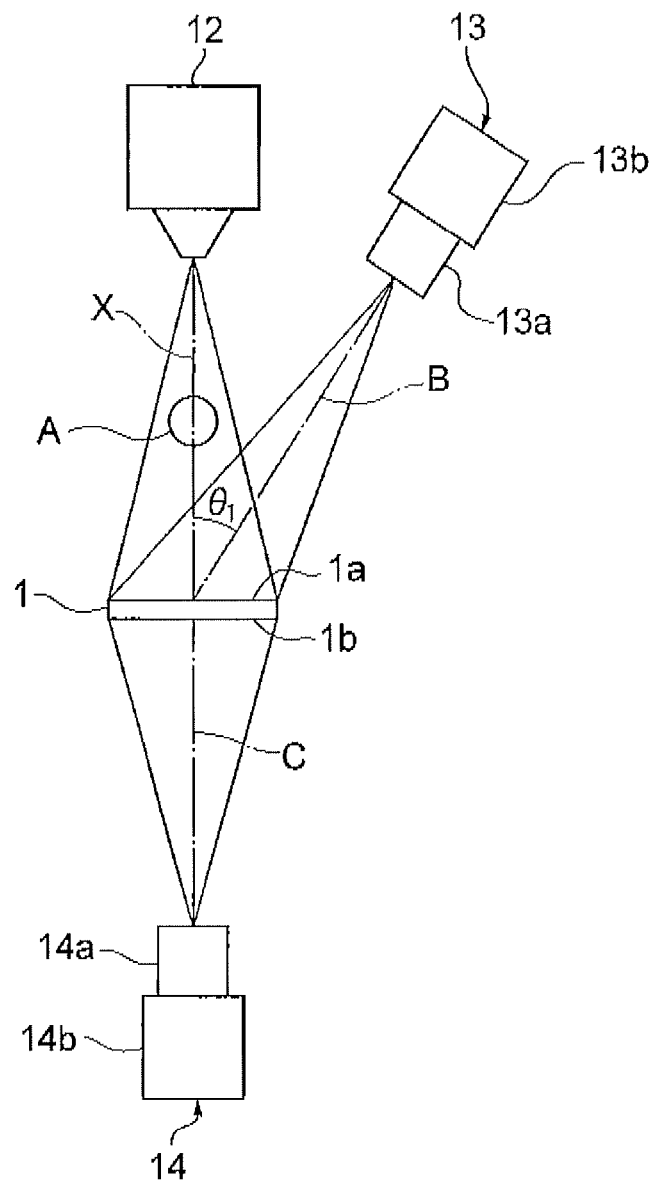
FIG. 3 is a front view showing an arrangement example of a radiation source 12 and detectors 13, 14 in the radiation image acquisition device 11 shown in FIG. 2.

Specifically, as shown in FIG. 3, the radiation source 12 may be arranged to face the object A and the detection surface 1a on the normal to the detection surface 1a and the front detector 13 may be arranged so that the optical axis B of the condensing lens unit 13a makes a predetermined angle $\theta_1$ ($0°<\theta_1<90°$) with respect to the normal to the detection surface 1a; that is, the front detector 13 may be arranged opposite to the detection surface 1a and off the normal to the detection surface 1a. In this case as well, no detector shadow is cast on the radiation transmission images, so as to suppress reduction of signal components. Furthermore, the front detector 13 is prevented from being exposed to the radiation and generation of noise is suppressed inside the front detector 13. In addition, the back detector 14 can acquire the radiation image without perspective, and the radiation image acquired by the front detector 13 can be corrected for perspective, using the radiation image acquired by the back detector 14 as a reference image, which facilitates the operation between the images on the detection surface 1a side and on the detection surface 1b side.

Figure 4:
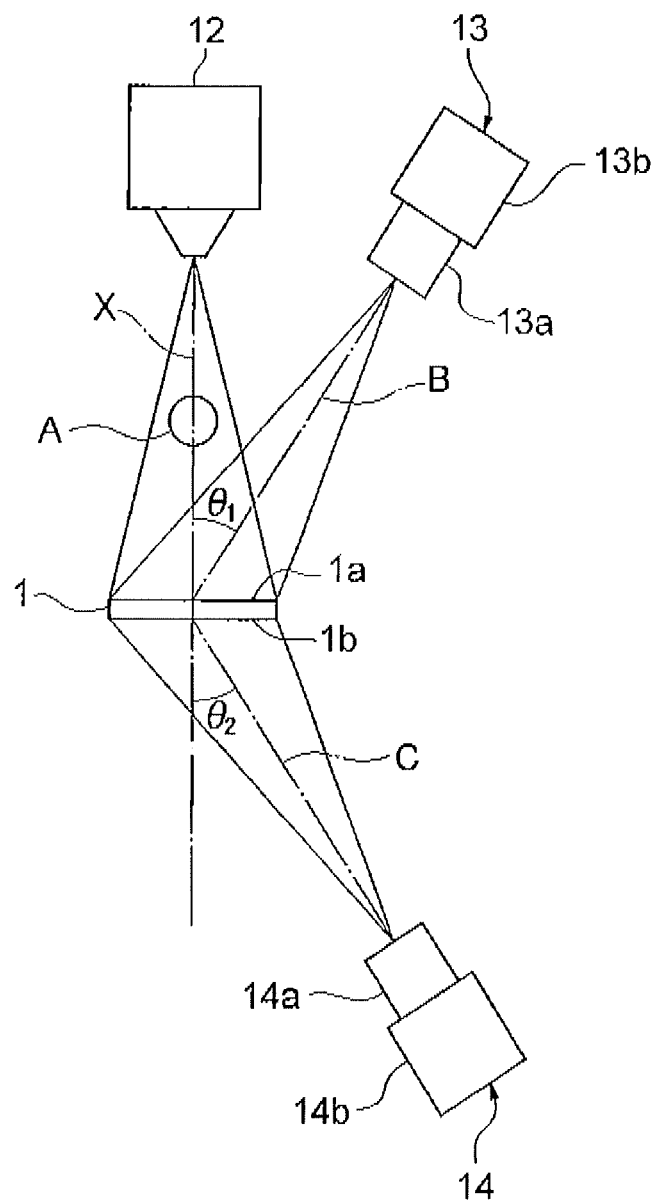
FIG. 4 is a front view showing another arrangement example of the radiation source 12 and detectors 13, 14 in the radiation image acquisition device 11 shown in FIG. 2.

As shown in FIG. 4, the back detector 14 may be arranged so that the optical axis C of the condensing lens unit 14a makes a predetermined angle $\theta_2$ ($0°<\theta_2<90°$) with respect to the normal to the detection surface 1b; that is, the back detector 14 may be arranged opposite to the detection surface 1b and off the normal to the detection surface 1b. In this case, the back detector 14 is also prevented from being exposed to the radiation and generation of noise is suppressed inside the back detector 14. In addition, the front detector 13 and the back detector 14 can acquire the radiation images with the same perspective, which facilitates the operation between the images on the detection surface 1a side and on the detection surface 1b side. For more facilitating the inter-image operation, it is desirable to make the angle $\theta_1$ and the angle $\theta_2$ equal to each other.

Figure 5:
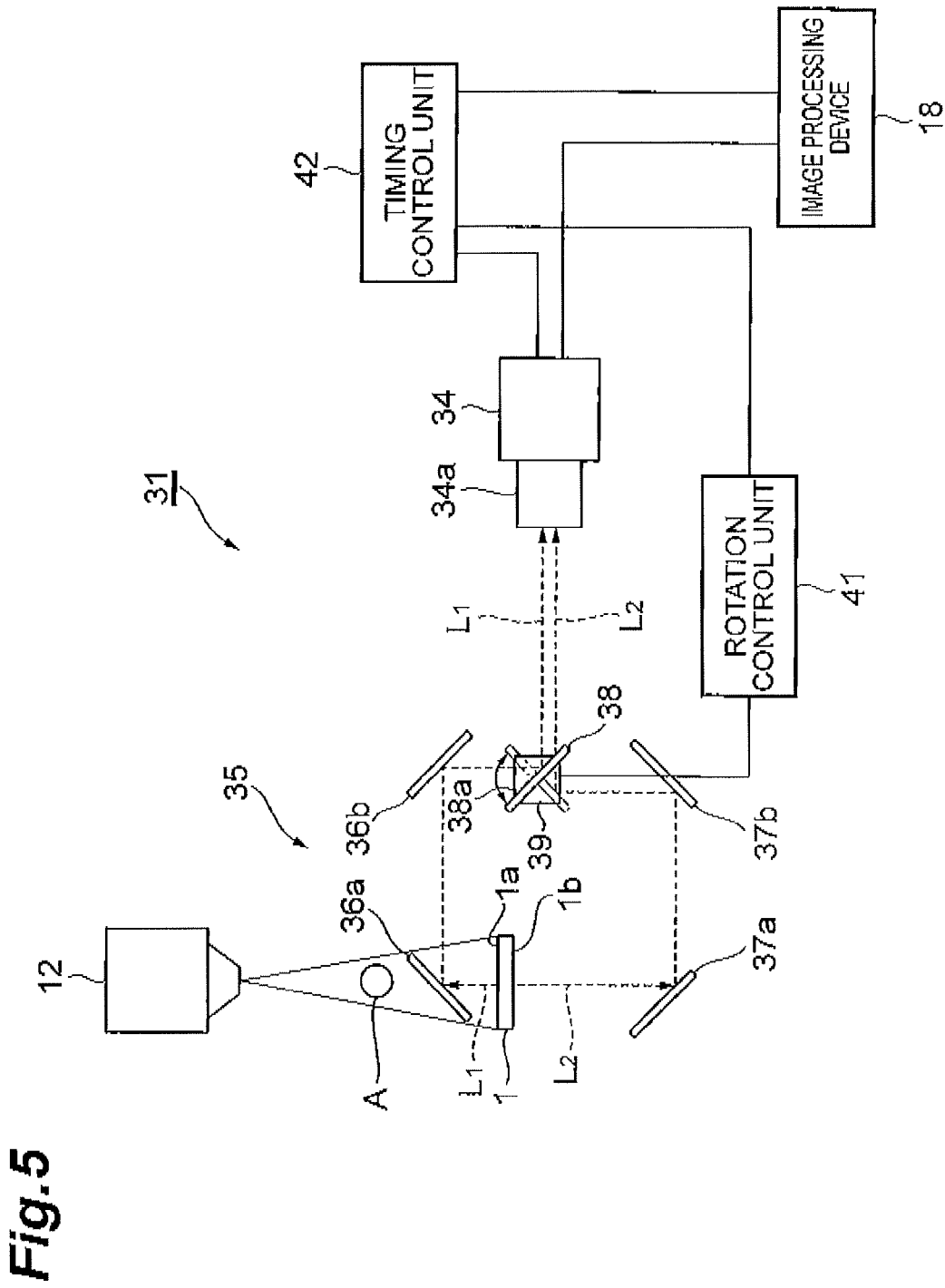
FIG. 5 is a schematic configuration diagram of another radiation image acquisition device 31 using the scintillator plate 1 shown in FIG. 1.

FIG. 5 is a schematic configuration diagram of another radiation image acquisition device 31 using the scintillator plate 1. The radiation image acquisition device 31 shown in the same drawing is a device that can acquire the low-energy image and the high-energy image by a single detector, and is provided with the radiation source 12, the scintillator plate 1 arranged so that the detection surface 1a thereof is approximately perpendicular to the emission direction of the radiation from the radiation source 12, a photodetector 34 which images light resulting from conversion by the scintillator plate 1, and an optical system 35 which guides the light resulting from the conversion by the scintillator plate 1, as radiation transmission images to the photodetector 34. This photodetector 34 is a detector of the indirect conversion method having a condensing lens unit 34a and an imaging unit 34b as the detectors 13, 14 in FIG. 2 are.

The optical system 35 is composed of five mirrors 36a, 36b, 37a, 37b, and 38 as optical members to control optical paths of the scintillation light emitted from the scintillator plate 1, and a rotary drive mechanism 39 to rotate the mirror 38. The mirrors 36a, 36b in the optical system 35 are arranged on the detection surface 1a side of the scintillator plate 1 and guide the scintillation light $L_1$ emitted from the detection surface 1a, to the mirror 38 arranged at a distant position along an extending direction of the detection surface 1a from the scintillator plate 1. The mirrors 37a, 37b in the optical system 35 are arranged on the detection surface 1b side of the scintillator plate 1 and guide the scintillation light $L_2$ emitted from the detection surface 1b, to the mirror 38. The mirror 38 in the optical system 35 is arranged so that a normal to a reflective surface 38a thereof is approximately parallel to a plane including the optical paths of the scintillation light $L_1$, $L_2$. The mirror 38 is supported so as to be rotatable around an axis approximately perpendicular to the plane including the optical paths of the scintillation light $L_1$, $L_2$ by the rotary drive mechanism 39 incorporating a motor. The mirror 38 supported by the rotary drive mechanism 39 as described above selectively guides the scintillation light $L_1$, $L_2$ toward the photodetector 34 arranged further away along the extending direction, of the detection surface 1a from the mirror 38. Namely, when the rotary drive mechanism 39 rotates the mirror 38 so as to make the reflective surface 38a face the mirror 36b (as indicated by a solid line in FIG. 1), the scintillation light $L_1$ is reflected toward the condensing lens unit 34a of the photodetector 34. On the other hand, when the rotary drive mechanism 39 rotates the mirror 38 so as to make the reflective surface 38a face the mirror 37b (as indicated by a double-dashed chain line in FIG. 1), the scintillation light $L_2$ is reflected toward the condensing lens unit 34a of the photodetector 34.

Furthermore, the radiation image acquisition device 31 is provided with a rotation control unit 41 for controlling rotation of the rotary drive mechanism 39, a timing control unit 42 for controlling timing of selection of the scintillation light $L_1$, $L_2$ by the mirror 38 and timing of imaging of the photodetector 34, and the image processing device 18 for processing image signals output from the photodetector 34. In more detail, the rotation control unit 41 sends a control signal to the rotary drive mechanism 39 in accordance with a command signal from the timing control unit 42 to control an angle of rotation of the mirror 38. The timing control unit 42 sends a command signal to the rotation control unit 41 to change over the rotation angle of the mirror 38 so as to reflect the scintillation light $L_1$ toward the photodetector 34, and at the same time, it sends a command signal to the photodetector 34 to image the scintillation light $L_1$ in synchronism with the changeover of the mirror 38. Furthermore, the timing control unit 42 sends a command signal to the rotation control unit 41 to change over the rotation angle of the mirror 38 so as to reflect the scintillation light $L_2$ toward the photodetector 34, and at the same time, it sends a command signal to the photodetector 34 to image the scintillation light $L_2$ in synchronism with the changeover of the mirror 38. The image processing device 18 acquires two image signals obtained as the result of the imaging of the scintillation light $L_1$, $L_2$ from the photodetector 34 and processes those two image signals to generate radiation transmission image data about the object A.

In the radiation image acquisition device 31 of this configuration, since the scintillation light beams $L_1$, $L_2$ emitted from the two surfaces of the scintillator plate 1 are guided via the optical system 35 to the photodetector 34, the photodetector 34 can be located apart from the radiation emission region. This arrangement prevents a shadow of the detector from being cast on the radiation projection images of the object A and also prevents the low-energy components of the radiation from being attenuated by the detector. There is also little direct conversion noise generated due to incidence of the radiation into the detector itself. Since the single detector can acquire the radiation transmission image of low energy components and the radiation transmission image of high energy components, it is easy to achieve downsizing of the device.

The below will describe the operational effect of the scintillator plate 1 described above.

Since in the scintillator plate 1 the two scintillators 3, 4 of the flat plate shape to convert radiation into scintillation light are arranged on both sides of the partition plate 2 of the planar shape which transmits the radiation, one scintillator 3 converts the radiation transmitted by the object A, into scintillation light and the other scintillator 4 converts the radiation after transmitted by the scintillator 3 and the partition plate 2, into scintillation light. At this time, the existence of the partition plate 2 makes the scintillation light beams generated in the two scintillators 3, 4, easier to be emitted from the surfaces 1a, 1b of the two scintillators 3, 4 on the opposite sides with respect to the partition plate 2. As a result, when this scintillator plate 1 is used in the radiation image acquisition device 11, 31 for condensing and imaging the scintillation light beams emitted from the two surfaces 1a, 1b of the scintillator plate 1, the high-energy radiation image and the low-energy radiation image can be efficiently separated.

Since the partition plate 2 has the property of blocking scintillation light, it can securely prevent the scintillation light generated in one of the scintillators 3, 4 from entering the other of the scintillators 3, 4 and thus can enhance the energy separation capability of radiation images.

When the wavelength conversion members highly sensitive to radiation in different energy bands are used as the materials of the scintillator 3 and the scintillator 4, the energy separation capability of radiation images can be more enhanced. Furthermore, when the thickness of the scintillator 3 is made different from the thickness of the scintillator 4, the detection sensitivities of radiation images in the different energy bands can be adjusted to each other, so as to simplify the image processing such as level correction.

It should be noted that the present invention is by no means intended to be limited to the foregoing embodiments.

Figure 6:
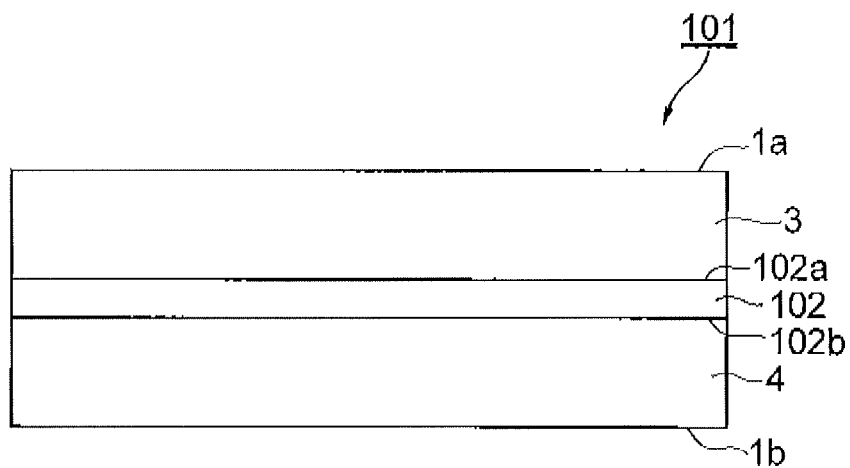
FIG. 6 is a front view of a scintillator plate according to a modification example of the present invention.

For example, like a scintillator plate 101 which is a modification example of the present invention shown in FIG. 6, a reflective surface 102a, or 102b to reflect the scintillation light generated by the scintillator 3 or 4 may be formed on each or either one of two surfaces of a partition plate 102. Such reflective surface 102a, 102b is formed on each or either one of the two surfaces of the partition plate 102 by evaporating aluminum thereon, by bonding a thin film of aluminum thereto, by coating the surface with metal particles transmitting radiation, in the thickness of not more than 0.1 μm, or by applying a white paint thereto. The reflective surface 102a, 102b may be formed by making the partition plate 102 itself of an aluminum plate or the like and mirror-polishing each or either one of two surfaces thereof. Furthermore, the reflective surface 102a, 102b may be arranged on each or either one of the two surfaces of the partition plate 102 by first forming the reflective surface 102a, 102b on the surface of the scintillator 3, 4 and then joining the scintillators 3, 4 to the partition plate 102. The configuration as described above allows the scintillator plate to securely prevent the scintillation light generated in one of the scintillators 3, 4 from entering the other scintillator 3 or 4 and also allows the radiation image acquisition device 11, 31 to efficiently detect the scintillation light. This allows acquisition of radiation images with high contrast while enhancing the energy separation capability of radiation images.

The partition plate 2 of the scintillator plate does not have to be limited to the one having the property of blocking the scintillation light generated in the scintillators 3, 4 but may be one having a filter function to block a partial wavelength region of the scintillation light. This configuration also allows the scintillator plate to efficiently separate the high-energy radiation image and the low-energy radiation image in desired ranges. Furthermore, the partition plate 2 is not limited to the one that transmits all the energy components of incident radiation, but may be one having a property of blocking radiation in a low energy region. In this case, incidence of the scintillation light generated by the radiation in the low energy region can be reduced in the scintillator 4 on the back side, which can further enhance the energy separation capability.

Preferably, the partition member has the property of blocking the scintillation light. The provision of the partition plate of this type can securely prevent the scintillation light generated in one wavelength conversion member from entering the other wavelength conversion member and thus enhance the energy separation capability of radiation images.

The partition plate is also preferably one wherein the reflective surface which reflects the scintillation light is formed. This configuration securely prevents the scintillation light generated in one wavelength conversion member from entering the other wavelength conversion member and enables efficient detection of the scintillation light by the image acquisition device. This makes it feasible to acquire the radiation images with high contrast while enhancing the energy separation capability of radiation images.

Furthermore, the first wavelength conversion member and the second wavelength conversion member are preferably formed of different materials. In this case, the use of the wavelength conversion members highly sensitive to radiation in different energy bands can farther enhance the energy separation capability of radiation images.

Yet furthermore, the first wavelength conversion member and the second wavelength conversion member preferably have different thicknesses. By adopting this configuration, it becomes feasible to adjust the detection sensitivities of radiation images in different energy bands to each other.

INDUSTRIAL APPLICABILITY

The present invention is applicable to the use as the scintillator plate for converting radiation transmitted by an object into scintillation light and enables observation of scintillation light emitted from a radiation entrance surface and a back surface behind it, thereby enabling acquisition of radiation detection images with a high energy separation capability.

REFERENCE SIGNS LIST 1, 101 scintillator plate; 2, 102 partition plate; 2a, 2b arrangement surfaces; 3, 4 scintillators; 11, 31 radiation image acquisition device; 102a, 102b reflective surfaces; A object.

The invention claimed is:
1. A scintillator plate which is a member of a flat plate shape to emit scintillation light according to incidence of the radiation transmitted by an object and which is used in an image acquisition device to condense and image the scintillation light, said scintillator plate comprising:
 a partition member of a planar shape configured to transmit radiation;

a first wavelength conversion member of a flat plate shape configured to be is arranged on one surface of the partition member and convert the radiation into scintillation light; and a second wavelength conversion member of a flat plate shape configured to be arranged on the other surface of the partition member and convert the radiation into scintillation light.

2. The scintillator plate according to claim 1,
wherein the partition member has a property of blocking the scintillation light.

3. The scintillator plate according to claim 1,
wherein a reflective surface configured to reflect the scintillation light is formed on the partition member.

4. The scintillator plate according to claim 1,
wherein the first wavelength conversion member and the second wavelength conversion member are made of different materials.

5. The scintillator plate according to 4 claim 1,
wherein the first wavelength conversion member and the second wavelength conversion member have different thicknesses.

6. A scintillator plate which is a member of a plate shape to emit scintillation light according to incidence of the radiation transmitted by an object and which is used in an image acquisition device to image the scintillation light, said scintillator plate comprising:

a partition member of a planar shape configured to transmit radiation;

a first wavelength conversion member of a plate shape configured to be arranged on one surface of the partition member and convert the radiation into scintillation light; and a second wavelength conversion member of a plate shape configured to be arranged on the other surface of the partition member and convert the radiation into scintillation light, wherein the partition member is manufactured by joining plate members on which the respective first and second wavelength conversion member are arranged, to each other on the side opposite to the respective first and second wavelength conversion member.

\* \* \* \* \*